(12) United States Patent
Suzuki (10) Patent No.: US 11,285,054 B2
(45) Date of Patent: Mar. 29, 2022

(54) ABSORBENT ARTICLE

(71) Applicant: DAIO PAPER CORPORATION, Ehime (JP)

(72) Inventor: Yoko Suzuki, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 647 days.

(21) Appl. No.: 16/301,909

(22) PCT Filed: Jun. 12, 2017

(86) PCT No.: PCT/JP2017/021594
§ 371 (c)(1),
(2) Date: Nov. 15, 2018

(87) PCT Pub. No.: WO2017/217358
PCT Pub. Date: Dec. 21, 2017

(65) Prior Publication Data
US 2019/0183688 A1 Jun. 20, 2019

(30) Foreign Application Priority Data
Jun. 14, 2016 (JP) .............................. JP2016-118081

(51) Int. Cl.
*A61F 13/15* (2006.01)
*A61F 13/475* (2006.01)
(Continued)

(52) U.S. Cl.
CPC ........ *A61F 13/4756* (2013.01); *A61F 13/472* (2013.01); *A61F 13/475* (2013.01);
(Continued)

(58) Field of Classification Search
CPC ................ A61F 13/4756; A61F 13/472; A61F 13/47218; A61F 13/47236; A61F 13/475;
(Continued)

(56) References Cited

U.S. PATENT DOCUMENTS

2006/0116652 A1* 6/2006 Miura .................. A61F 13/533
604/380
2008/0119810 A1* 5/2008 Kuroda ............. A61F 13/15707
604/379
(Continued)

FOREIGN PATENT DOCUMENTS

EP 2380541 10/2011
JP 2001-178775 7/2001
(Continued)

OTHER PUBLICATIONS

International Search Report for PCT/JP2017/021594 dated Jul. 4, 2017.
(Continued)

*Primary Examiner* — Jacqueline F Stephens
(74) *Attorney, Agent, or Firm* — IPUSA, PLLC (57) ABSTRACT

(Object) To prevent leakage of body fluids and to readily transmit pressure from both sides to a center portion in a width direction by bringing an absorbent article into close contact with a crotch area extending from a body fluid discharge portion to a start position of the intergluteal cleft. (Means of Achieving the Object) A pair of right and left compressed grooves (8, 8) that extend in an approximately longitudinal direction is formed on a surface of a liquid permeable top sheet (3). The compressed grooves (8) have separation distance reduced regions (11), in which a separation distance between the right and left compressed grooves is reduced, formed at the back of a region corresponding to a body fluid discharge portion (H) of a wearer, and also have vastly enlarged portions (10), in which widths of the compressed grooves (8) are enlarged, formed at positions within the separation distance reduced regions (11) and where the separation distance between the right and left compressed grooves (8, 8) becomes minimum.

5 Claims, 6 Drawing Sheets

(51) Int. Cl.
*A61F 13/472* (2006.01)
*A61F 13/533* (2006.01)
*A61F 13/511* (2006.01)
*A61F 13/514* (2006.01)
*A61F 13/53* (2006.01)

(52) U.S. Cl.
CPC .... *A61F 13/4752* (2013.01); *A61F 13/47218* (2013.01); *A61F 13/47236* (2013.01); *A61F 13/514* (2013.01); *A61F 13/51108* (2013.01); *A61F 13/53* (2013.01); *A61F 13/533* (2013.01); *A61F 2013/51186* (2013.01)

(58) Field of Classification Search
CPC ............ A61F 13/4752; A61F 13/51108; A61F 13/514; A61F 13/53; A61F 13/533; A61F 2013/51186
USPC .......................... 604/378, 379, 380, 385.101
See application file for complete search history.

(56) References Cited

U.S. PATENT DOCUMENTS

| | | | |
|---|---|---|---|
| 2008/0281287 A1* | 11/2008 | Marcelo | A61F 13/4756 604/383 |
| 2009/0240225 A1* | 9/2009 | Noda | A61F 13/474 604/378 |
| 2011/0251575 A1 | 10/2011 | Kuroda et al. | |
| 2011/0288514 A1* | 11/2011 | Kuroda | A61F 13/533 604/380 |
| 2016/0143790 A1 | 5/2016 | Umemoto | |

FOREIGN PATENT DOCUMENTS

| | | |
|---|---|---|
| JP | 2010-148706 | 7/2010 |
| WO | 2012/105533 | 8/2012 |
| WO | 2014/208729 | 12/2014 |
| WO | 2015/072502 | 5/2015 |

OTHER PUBLICATIONS

Extended European Search Report for 17813254.4 dated Mar. 14, 2019.

* cited by examiner

ABSORBENT ARTICLE

TECHNICAL FIELD

The present invention generally relates to an absorbent article used for a sanitary napkin, a panty liner, an incontinence pad, or toiletry, and specifically relates to an absorbent article having compressed grooves recessed from a skin contact surface side toward a non-skin side.

BACKGROUND ART

Conventionally, as absorbent articles such as a panty liner, a sanitary napkin, and an incontinence pad, an absorbent article that includes an absorbent body made of cotton-like pulp and interposed between a liquid impermeable back sheet such as a polyethylene sheet or a polyethylene-sheet-laminated non-woven fabric and a liquid permeable top sheet such as a non-woven fabric or a liquid permeable plastic sheet is known.

Among such absorbent articles, an absorbent article for nighttime use is continuously attached for a long period of time, thus placing importance on preventing leakage. For this type of absorbent article, various improvements have been made and a variety of measures have been taken to prevent leakage of body fluids. For example, with the aim of preventing body fluids from spreading sideways while also preventing an absorbent body from being twisted, and of causing a center portion of the absorbent body to protrude so as to bring the absorbent body into close contact with a part of the body, there is a technique that forms a compressed groove on a skin contact surface by heat embossing in such a manner that the compressed groove is recessed from the outer surface of a liquid permeable top sheet toward a non-skin side (toward a liquid impermeable back sheet).

In recent years, various absorbent articles have been developed in which compressed grooves are shaped to fit the body. For example, an embodiment illustrated in FIG. 5 and FIG. 6 of Patent Document 1 below discloses an absorbent article in which a width (W1) of a compressed groove located in a region between approximately transverse high-compressed portions becomes smaller than a width (W2) of the compressed groove where an approximately transverse compressed portion is located. The approximately transverse high-compressed portions are formed so as to almost fully traverse the compressed groove in the width direction and disposed at intervals in the longitudinal direction.

Further, an embodiment illustrated in FIG. 4 of Patent Document 2 below discloses an absorbent article in which an anti-leakage groove has the maximum width in a region making contact with a discharge portion of a wearer.

RELATED-ART DOCUMENTS

Patent Documents

[Patent Document 1] Japanese Unexamined Patent Application Publication No. 2010-148706
[Patent Document 2] Japanese Unexamined Patent Application Publication No. 2001-178775

SUMMARY OF THE INVENTION

Problem to be Solved by the Invention

The absorbent article disclosed in Patent Document 1 above provides a compressed groove having relatively wider portions and relatively narrower portions, aiming to decrease the stiffness of the relatively narrower portions, and thus improve wearability. However, because of the decreased stiffness of the relatively narrower portion, there is a problem in that legs pressure, which is exerted inwardly from both sides of the absorbent article, is not sufficiently transmitted to the inner side of the absorbent article and a center portion of the absorbent body fails to readily protrude toward the skin side.

Further, in the absorbent article disclosed in Patent Document 2 above, the anti-leakage groove is formed so as to have the maximum width in the region making contact with the discharge portion of the wearer. Thus, in the region making contact with the discharge portion, it is assumed that leg pressure, which is exerted inwardly from both sides of the absorbent article, is readily transmitted to the inner side of the absorbent article and the inner side of the absorbent body readily protrudes to the skin side; however, because the wider portion of the anti-leakage groove is formed in the nearly entire region making contact with the discharge portion, there is a possibility that the hardness of the anti-leakage groove may cause wearability to become worse and the absorbent article to not readily curve following the roundness of the body in the front and back direction.

Further, in the above absorbent articles disclosed in Patent Documents 1 and 2, it is difficult to say that a problem relating to close contact with buttocks is sufficiently solved. Accordingly, it has been desired to develop a technique that eliminates a gap between an absorbent article and buttocks so as to prevent body fluids from leaking from the buttocks side.

In particular, when discharged body fluids flow backward, the body fluids first pass through a crotch area extending from a body fluid discharge portion to a start position of the intergluteal cleft. Therefore, it is considered that an effective way to prevent leakage from the back is to bring an absorbent article into close contact with the skin surface in this area and absorb body fluids flowing backward.

Also, in such a conventional absorbent article, compressed grooves are often formed in a linear shape with approximately the same width by means of embossing and are located outside the periphery of a raised center portion of the absorbent article. Such compressed grooves are formed with the aim of transmitting leg pressure or buttocks pressure, which is exerted inwardly from both sides in the width direction, to the inner side of the absorbent article so as to cause a center portion of the absorbent body located between the compressed grooves to protrude toward the skin side, and also with the aim of maintaining the shape of the raised center portion that has an increased thickness toward the skin side and is disposed at an approximately center area of the absorbent body.

However, in a case where a compressed groove is formed in a linear shape with approximately the same width, leg pressure transmitted from the sides to the center portion of the absorbent body tends to be dispersed. Thus, it is difficult to cause a specific part of the absorbent body to protrude toward the skin side. There is also a problem in that pressure fails to be transmitted to the center portion of the absorbent body, because the compressed groove is partially bent or collapsed when leg pressure is exerted from the sides in the width direction.

It is a general object of the present invention to provide an absorbent article that prevents leakage of body fluids while readily transmitting pressure from sides to a center portion by bringing the absorbent article into close contact with a crotch area extending from a body fluid discharge portion to a start position of the intergluteal cleft of a wearer.

Means to Solve the Problem

In light of the above-described problems, the invention described in claim 1 provides an absorbent article including an absorbent body interposed between a liquid impermeable back sheet and a liquid permeable top sheet, a pair of right and left compressed grooves that extend in an approximately longitudinal direction being formed on a surface of the liquid permeable top sheet, wherein the right and left compressed grooves have separation distance reduced regions, in which a separation distance between the right and left compressed grooves is reduced, formed at back of a region corresponding to a body fluid discharge portion of a wearer, and also have vastly enlarged portions, in which widths of the compressed grooves are enlarged, formed at positions within the separation distance reduced regions and where the separation distance between the right and left compressed grooves becomes minimum.

According to the invention described in claim 1, the right and left compressed grooves that extend in the approximately longitudinal direction and are formed on the surface of the liquid permeable top sheet have, in their middle portions, the vastly enlarged portions in which the widths of the compressed grooves are enlarged. Also, separation distance reduced regions in which a separation distance between the right and left compressed grooves is reduced are formed at the back of a region corresponding to a body fluid discharge portion of a wearer. The vastly enlarged portions are formed at positions within the separation distance reduced regions and where the separation distance between the right and left compressed grooves becomes minimum. Accordingly, when leg pressure or buttocks pressure is exerted inwardly from the sides in the width direction at a time when the absorbent article is worn, pressure tends to be applied to the separation distance reduced regions of the compressed grooves that are curved inward in the width direction. Also, the pressure applied to the separation distance reduced regions is concentrated in the vastly enlarged portions that are formed at the minimum distance positions of the separation distance reduced regions. The vastly enlarged portions serve as bases for transmitting the pressure to a center portion of the absorbent body, and thus, the absorbent body located between the right and left compressed grooves readily protrudes toward the skin side, with the center portion of the absorbent body located between the vastly enlarged portions as the highest point. Accordingly, the center portion protruding toward the skin side is brought into close contact with the skin surface in the crotch area extending from the body fluid discharge portion to the start position of the intergluteal cleft of the wearer. This allows body fluids, discharged from the body fluid discharge portion and flowing backward along the skin surface, to be securely absorbed, and allows leakage from the back to be prevented.

According to the invention described in claim 2, the absorbent article described in claim 1 is provided, where the vastly enlarged portions are formed such that both side walls of each of the compressed grooves are projected outward or only one of the side walls is projected outward.

According to the invention described in claim 2, the vastly enlarged portions are formed by causing the both side walls of each of the compressed grooves to be projected outward or one of the side walls to be projected outward. In each of the vastly enlarged portions formed in the above-described manner, a portion projected toward the outside more than the connected compressed groove in the width direction of the absorbent article serves to receive leg pressure exerted from outside in the width direction, and causes the pressure to be concentrated in the corresponding vastly enlarged portion. Also, a portion projected toward the inside in the width direction of the absorbent article serves as a base for pushing the absorbent body located between the right and left compressed grooves inward.

According to the invention described in claim 3, the absorbent article described in claim 1 or 2 is provided, where the vastly enlarged portions each have at least two protruding portions that protrude toward the inside in the width direction of the absorbent article.

According to the invention described in claim 3, the at least two protruding portions that protrude toward inside in the width direction of the absorbent article tend to serve as bases for transmitting pressure to the center portion of the absorbent body.

According to the invention described in claim 4, the absorbent article described in any one of claims 1 to 3 is provided, where the vastly enlarged portions are each formed in an approximately star shape in planar view.

According to the invention described in claim 4, by forming each of the vastly enlarged portions in an approximately star shape in planar view, the protruding portions that protrude toward inside in the width direction of the absorbent article can be formed at at least two positions, and also a favorable appearance design can be provided.

Effects of the Invention

According to the invention as described above, an absorbent article can be brought into close contact with a crotch area extending a body fluid discharge portion to a start position of the intergluteal cleft of a wearer, such that leakage of body fluids can be prevented and pressure from both sides in the width direction can be readily transmitted to a center portion.

BRIEF DESCRIPTION OF THE DRAWINGS

FIGS. 6 (A) and (B) are plan views (part 1) illustrating a variation of the vastly enlarged portions 20;

FIGS. 7 (A) and (B) are plan views (part 2) illustrating a variation of the vastly enlarged portions 20;

MODE FOR CARRYING OUT THE INVENTION

In the following, embodiments of the present invention are described below with reference to the accompanying drawings.

[Basic Structure of Sanitary Napkin 1]

Figure 1:
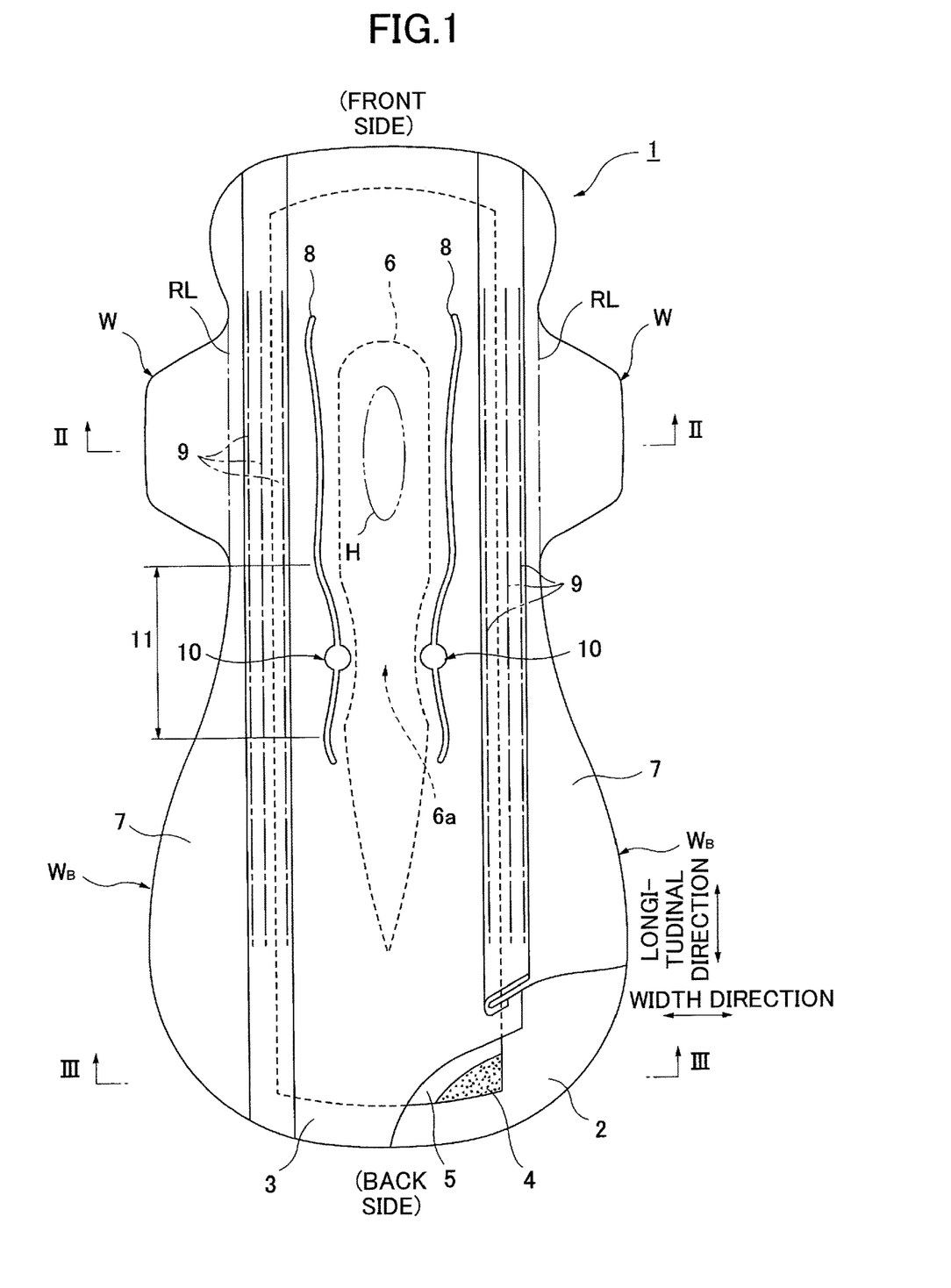
FIG. 1 is a partially expanded cutaway view of a sanitary napkin 1.
Figure 2:
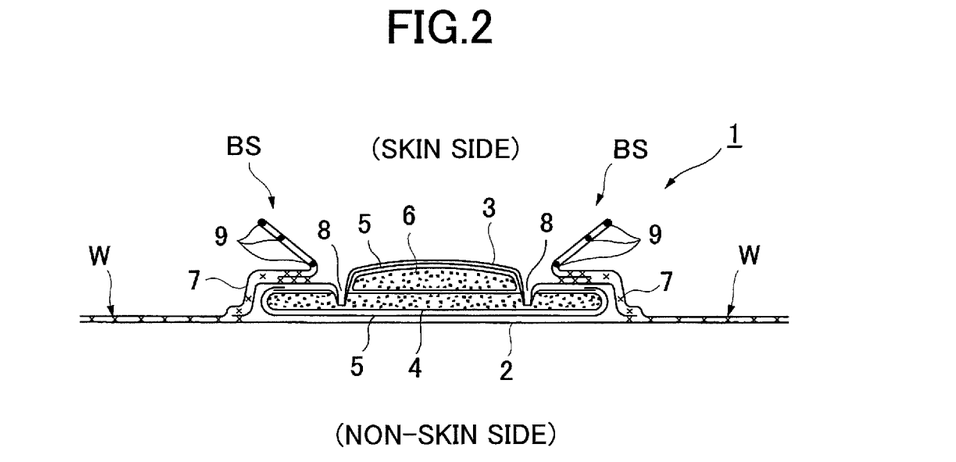
FIG. 2 is a cross-sectional view taken along a line II-II of FIG. 1.
Figure 3:
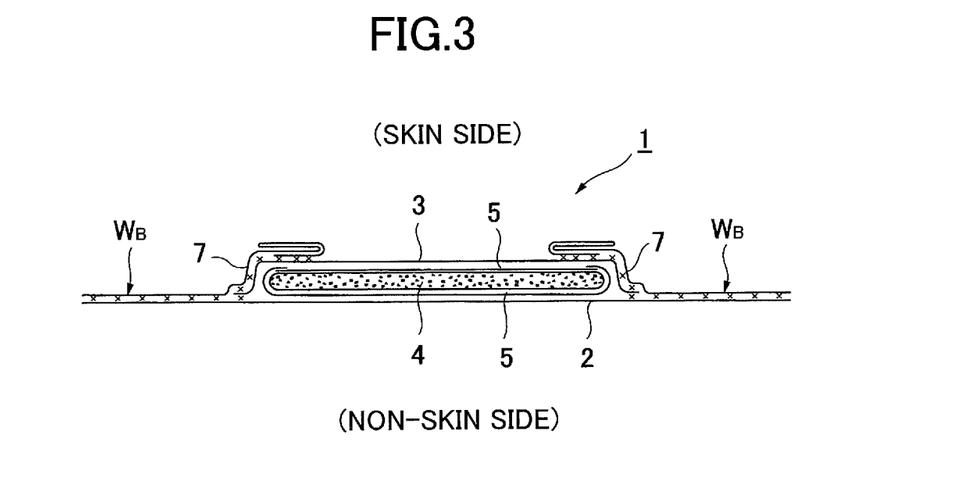
FIG. 3 is a cross-sectional view taken along a line III-III of FIG. 1.

As illustrated in FIGS. 1 through 3, a sanitary napkin 1 according to the present invention includes: a liquid impermeable back sheet 2 formed of a polyethylene sheet, for example; a liquid permeable top sheet 3 that allows menstrual blood, vaginal discharge, and the like (hereinafter also collectively referred to as body fluids) to quickly pass through; an absorbent body 4 interposed between the sheets 2 and 3 and made of cotton-like pulp or synthetic pulp, for example; and a side non-woven fabric 7 provided over the approximately entire length of each side of a skin contact surface along a longitudinal direction. At front and back end portions of the absorbent body 4, outer end portions of the liquid impermeable back sheet 2 and the liquid permeable top sheet 3 are bonded to each other with an adhesive such as a hot-melt adhesive or with an adhesive means such as a heat seal or an ultrasonic seal. Furthermore, at each side of the absorbent body 4, the liquid impermeable back sheet 2 and the side non-woven fabric 7 that laterally extend longer than the absorbent body 4 are bonded to each other with an adhesive such as a hot-melt adhesive or with an adhesive means such as a heat seal and an ultrasonic seal. As a result, flaps without the absorbent body are formed. In the illustrated example, in order to maintain the shape of the absorbent body 4 and to improve diffusivity thereof, the absorbent body 4 is surrounded by an encapsulating sheet 5 made of a crepe paper sheet or a non-woven fabric; however, the encapsulating sheet 5 is not necessarily provided. Although not illustrated, a second sheet formed of a hydrophilic non-woven fabric and having approximately the same shape as the liquid permeable top sheet 3 may be disposed facing a non-skin side of the liquid permeable top sheet 3.

In the following, the structure of the sanitary napkin 1 will be described in more detail. The liquid impermeable back sheet 2 uses a sheet material such as polyethylene having at least a water shielding property. In addition, in terms of stuffiness prevention, a material having moisture permeability is preferably used. As such a water shielding and permeable sheet material, a microporous sheet is preferably used. The microporous sheet is obtained by forming a sheet by melting and kneading inorganic filler with olefin resin such as polyethylene and polypropylene, and subsequently stretching the sheet in one axial direction or two axial directions. On a non-skin side (an outer surface) of the liquid impermeable back sheet 2, one or more adhesive layers (not illustrated) are formed along the longitudinal direction of the napkin such that the sanitary napkin 1 is fixed to underwear when worn. As the liquid impermeable back sheet 2, a polyethylene laminate non-woven fabric having a plastic film and a non-woven fabric layered on each other may be used.

Next, as the liquid permeable top sheet 3, a perforated or an imperforated non-woven fabric, a porous plastic sheet, or the like is preferably used. Examples of a material fiber forming the non-woven fabric include synthetic fibers such as an olefin-based synthetic fiber such as polyethylene or polypropylene, a polyester-based synthetic fiber, and a polyamide-based synthetic fiber, regenerated fibers such as rayon and cuprammonium rayon, and natural fibers such as cotton. Further, as the liquid permeable top sheet 3, a non-woven fabric obtained by applying an appropriate processing method such as a spunlace method, a spunbond method, a thermal bond method, a melt blown method, or a needle punch method to any of the above-described material fibers may be used. Among these processing methods, the spunlace method is superior in terms of flexibility, the spunbond method is superior in terms of drape properties, and the thermal bond method is superior in terms of bulkiness and compression restorability. When a number of through-holes are formed on the liquid permeable top sheet 3, body fluids can become quickly absorbed, providing a wearer with an excellent dry touch. Although either a long fiber or a short fiber may be used as the non-woven fabric, it is preferable to use a short fiber in order to provide texture of towel cloth. Further, in order to facilitate an embossing process, an olefin-based fiber such as polyethylene or polypropylene having a relatively low melting point may be used. Further, a composite fiber such as a core-in-sheath fiber having a high-melting-point fiber as a core and a low-melting-point fiber as a sheath, a side-by-side fiber, or a split fiber may be preferably used.

The absorbent body 4 interposed between the liquid impermeable back sheet 2 and the liquid permeable top sheet 3 is formed of, for example, cotton-like pulp and a water-absorptive polymer. The water-absorptive polymer is mixed, for example, as a granular powder, into the pulp that forms the absorbent body. Examples of the pulp include chemical pulp made from wood, cellulose fibers such as dissolving pulp, and synthetic cellulose fibers such as rayon and acetate. In terms of function and price, softwood pulp with a long fiber length is more preferably used than hardwood pulp. The weight per unit area of the absorbent body 4 is 250 to 650 $g/m^2$, and is more preferably 300 to 400 $g/m^2$.

Further, a synthetic fiber may be mixed into the absorbent body 4. Examples of the synthetic fiber that may be used include polyolefin-based fibers such as polyethylene and polypropylene, polyester-based fibers such as polyethylene terephthalate and polybutylene terephthalate, polyamide-based fibers such as nylon, and a copolymer thereof. Also, a mixture of two types of the above-described fibers may be used. Further, a composite fiber such as a core-in-sheath fiber having a high-melting-point fiber as a core and a low-melting-point fiber as a sheath, a side-by-side fiber, or a split fiber may be used. Also, a mixture of two types of the above-described fibers may be used. Further, a composite fiber such as a core-in-sheath fiber having a high-melting-point fiber as a core and a low-melting-point fiber as a sheath, a side-by-side fiber, or a split fiber may be used. In order to have hydrophilicity with body fluids, the synthetic fiber preferably undergoes surface treatment by using, for example, a hydrophilizing agent when a hydrophobic fiber is used.

As illustrated in FIG. 1 and FIG. 2, a raised center portion 6 having an increased thickness toward the skin side is preferably provided in an area including a region corresponding to a body fluid discharge portion H of the absorbent body 4. The raised center portion 6 is located at a skin-side surface of the absorbent body 4, and is provided at a center portion in the width direction of the absorbent body 4. The raised center portion 6 has a width dimension and a longitudinal dimension smaller relative to those of the absorbent body 4. If the thickness of the raised center portion 6 is too large, stiffness increases, causing the raised center portion 6 to not sufficiently fit the body. If the thickness of the raised center portion 6 is too small, the raised center portion 6 does not sufficiently make close contact with the body fluid discharge portion H. Accordingly, the thickness of the raised center portion 6 is 3 to 25 mm, and is preferably 5 to 18 mm. Also, the total weight per unit area of the raised center portion 6 and the part of the absorbent body 4 where the raised center portion 6 is provided is preferably 400 to 900 $g/m^2$, and is more preferably 600 to 800 $g/m^2$.

The raised center portion 6 is provided in an area including the region corresponding to at least the body fluid discharge portion H of the wearer. The raised center portion 6 may be formed into an elongated shape that continues from the area including the region corresponding to the body fluid discharge portion H to an area including a region corresponding to the intergluteal cleft of the wearer. Alternatively, the raised center portion 6 may be disposed only in the area including the region corresponding to the body fluid discharge portion H, and is not necessarily provided in the backward area including the region corresponding to the intergluteal cleft.

As illustrated in FIG. 1, when the raised center portion 6 is formed into the elongated shape, which continues from the area including the region corresponding to the body fluid discharge portion H to the area including the region corresponding to the intergluteal cleft, a narrow width portion 6a, whose outline on each side is curved inward in the width direction, is preferably formed at the back of the region corresponding to the body fluid discharge portion H. By forming the narrow width portion 6a, the raised center portion 6 tends to fit a small recess or projection formed on the skin surface extending from the back end of the body fluid discharge portion H to the start position of the intergluteal cleft of the wearer, thereby enhancing close contact with the skin surface.

The raised center portion 6 includes at least a pulp fiber and a synthetic fiber. The pulp fiber and synthetic fiber are mixed at a ratio ranging from 80:20 to 20:80 in terms of weight, and are preferably mixed at a ratio ranging from 40:60 to 60:40 in terms of weight. Further, the raised center portion 6 may also include a water-absorptive polymer. Examples of the water-absorptive polymer include a polyacrylate cross-linked product, a self-crosslinked polyacrylic acid salt, an acrylic acid ester-vinyl acetate copolymer cross-linked saponified product, an isobutylene-maleic anhydride copolymer cross-linked product, a polysulfone salt cross-linked product, and a product obtained by partially cross-linking a water-swellable polymer such as polyethylene oxide or polyacrylamide. Among them, an acrylic acid or an acrylic acid salt, which is excellent in absorbed amount and water absorption rate, is preferable. For such a water-absorptive polymer having the above-described water absorption performance, it is possible to adjust the absorption power and the water absorption rate by adjusting the cross-linking density and the cross-linking density gradient in a manufacturing process. Because the raised center portion 6 promotes permeation into the absorbent body 4, what is known as gel blocking occurs when the content of the water-absorptive polymer is large. Thus, the content of the water-absorptive polymer in terms of weight is preferably 1% to 10% of the total weight of the pulp fiber and the synthetic fiber. When the content of the water-absorptive polymer exceeds 50%, the fibers become not entangled, decreasing the strength of the sheet and causing the sheet to be ripped or cracked. Thus, the water-absorptive polymer content of more than 50% is not desired.

As illustrated in the cross-sectional views of FIG. 2 and FIG. 3, a width dimension of the liquid permeable top sheet 3 is slightly larger than a width of the absorbent body 4 so as to cover the absorbent body 4. The side non-woven fabric 7, formed of a different material from the liquid permeable top sheet 3, is provided outside the liquid permeable top sheet 3. To be more specific, the side non-woven fabric 7 is formed of a non-woven fabric material to which appropriate water-repellency treatment or hydrophilic treatment is applied, depending on the purpose such as preventing menstrual blood or vaginal discharge from permeating or enhancing texture. As the side non-woven fabric 7, a sheet that uses a synthetic fiber or a regenerated fiber as a material and is formed by an appropriate processing method may be used. Preferably, in order to prevent stuffiness while eliminating friction with the skin, a non-woven fabric having air permeability with a reduced basis weight may be used as the side non-woven fabric 7. Preferably, in order to prevent stuffiness while eliminating friction with the skin, a non-woven fabric having air permeability with a reduced basis weight may be used as the side non-woven fabric 7. To be more specific, a non-woven fabric with a basis weight of 13 to 23 $g/m^2$ is desirably used. Further, in order to securely prevent body fluids from permeating, a water-repellent non-woven fabric coated with a silicon-based, a paraffin-based, or an alkyl-chromic-chloride-based water-repellent agent is preferably used.

As illustrated in FIG. 2 and FIG. 3, on each outer side of the sanitary napkin relative to the middle portion in the width direction, the side non-woven fabric 7 is bonded from an inward position to an outer edge of the liquid impermeable back sheet 2 with an adhesive such as a hot-melt adhesive. The layered sheet portions of the liquid impermeable back sheet 2 and each of the side non-woven fabrics 7 form flaps on both sides of the absorbent body 4, without the absorbent body 4 being interposed. The flaps may include a pair of right and left wing-shaped flaps W, W at positions alongside the body fluid discharge region H of the absorbent body 4, and may also include hip-holding flaps WB, WB on the buttocks side (back side) relative to the wing-shaped flaps W, W. Outer surfaces of the wing-shaped flaps W, W and the hip-holding flaps WB, WB have adhesive layers (not illustrated). When the sanitary napkin is attached to underwear, the wing-shaped flaps W, W are folded back at positions of fold-back lines RL so as to be fixed to a crotch portion of the underwear, and also the hip-holding flaps WB, WB are fixed to an inner surface of the underwear.

An inner side of the side non-woven fabric 7 is folded back to be almost two-fold, and one or a plurality of (in the illustrated example, three) threadlike elastic expansion and contraction members 9, 9 are provided inside this double sheet. The ends Or appropriate positions in the longitudinal direction of each of the elastic expansion and contraction members 9, 9 are fixed at a middle portion in the height direction of the double sheet. In a layered state in which the double sheet is folded outward once, the front and back ends of the double sheet is bonded to the absorbent body 4 side as illustrated in FIG. 3. Accordingly, right and left three-dimensional linear gathers BS, BS standing toward the skin side while being sloped outward are formed as illustrated in FIG. 2.

[Compressed Grooves]

In the sanitary napkin 1, compressed grooves 8 that are recessed from a skin contact surface side (an outer surface side of the liquid permeable top sheet 3) toward a non-skin side (a liquid impermeable back sheet 2 side) are formed outside of and in the vicinity of the raised center portion 6. The compressed grooves 8 are formed on each side extending from the area including the region corresponding to at least the fluid discharge portion H to the area including the region corresponding to the intergluteal cleft. The area including the region corresponding to the fluid discharge portion H refers to a center area in the width direction that includes the entire region with which the body fluid discharge portion H of the wearer makes contact when the sanitary napkin 1 is worn. For the sanitary napkin 1 provided with wing-shaped flaps W at the sides, the length of the area including the region corresponding to the fluid discharge portion H in the longitudinal direction of the sanitary napkin 1 approximately corresponds to a lengthwise range of the wing-shaped flaps W, W. Also, the area including the region corresponding to the intergluteal cleft refers to a center area in the width direction that covers at least a part of the intergluteal cleft of the wearer when the sanitary napkin 1 is worn, and more specifically refers to a crotch area extending backwardly from the start position to the middle position of the intergluteal cleft.

The compressed grooves 8 have separation distance reduced regions 11 in which a separation distance between the right and left compressed grooves are reduced. The separation distance reduced regions 11 are formed at the back of the region corresponding to the body fluid discharge portion H. Also, the compressed grooves 8 have vastly enlarged portions 10 in which widths of the right and left compressed grooves are vastly enlarged. The vastly enlarged portions 10 are formed at positions within the separation distance reduced regions 11 and where the widths of the right and left compressed grooves 8, 8 become minimum.

The vastly enlarged portions 10 are portions each formed in the middle of the corresponding compressed groove 8 by vastly enlarging the both side walls. Also, the vastly enlarged portions 10 are each formed continuously from the connected compressed groove 8 without being separated from the connected compressed groove 8 and each have approximately the same depth as that of the connected compressed groove 8. Further, each of the compressed grooves 8 can be curved approximately at the same curvature before and after the corresponding vastly enlarged portion 10, without being separated or bent at the corresponding vastly enlarged portion 10 provided in the middle. Also, the compressed grooves 8, 8 each have approximately the same width before and after the corresponding vastly enlarged portion 10 along the entire length.

The separation distance reduced regions 11 are regions each formed by making a separation distance between the right and left compressed grooves 8, 8 in the width direction of the sanitary napkin relatively smaller than at the front and back regions. The separation distance reduced regions 11 are formed by causing the right and left compressed grooves 8, 8 to be curved inward in the width direction. The separation distance reduced regions 11 are preferably formed along the outline of the narrow width portion 6a that is formed at the back of the region corresponding to the body fluid discharge portion H of the raised center portion 6. To be more specific, as illustrated in FIG. 1, the separation distance reduced regions 11 are each provided at a position extending from the back of the region corresponding to the body fluid discharge portion H to the start position of the intergluteal cleft of the wearer. The length of each of the separation distance reduced regions 11 in the longitudinal direction of the sanitary napkin extends from the back end of the wing-shaped flap W to the front of the hip-holding flaps WB. Specifically, the length of each of the separation distance reduced regions 11 in the longitudinal direction of the sanitary napkin, from the back end of the wing-shaped flap W towards the back direction, is 40 to 70 mm, and is preferably 50 to 60 mm. By making the separation distance between the compressed grooves 8, 8 smaller in this region, it becomes readily possible for leg pressure or the buttocks pressure exerted from the both sides of the sanitary napkin to act as pressure for causing the center portion of the absorbent body to protrude toward the skin side, along the shape of the inwardly curved compressed grooves 8. Accordingly, it becomes possible to enhance close contact with the skin. The narrow width portion 6a of the raised center portion 6 provided immediately inside the separation distance reduced regions 11 is formed such that the outline of the narrow width portion 6a is curved along the curved shapes of the separation distance reduced regions 11. The minimum width of the narrow width portion 6a is preferably 20 to 40 mm. Accordingly, the center portion readily makes close contact with the skin side when protruding toward the skin side upon leg pressure being exerted at a time of wearing the sanitary napkin. Thus, body fluids flowing along the skin can be securely absorbed.

Figure 4:
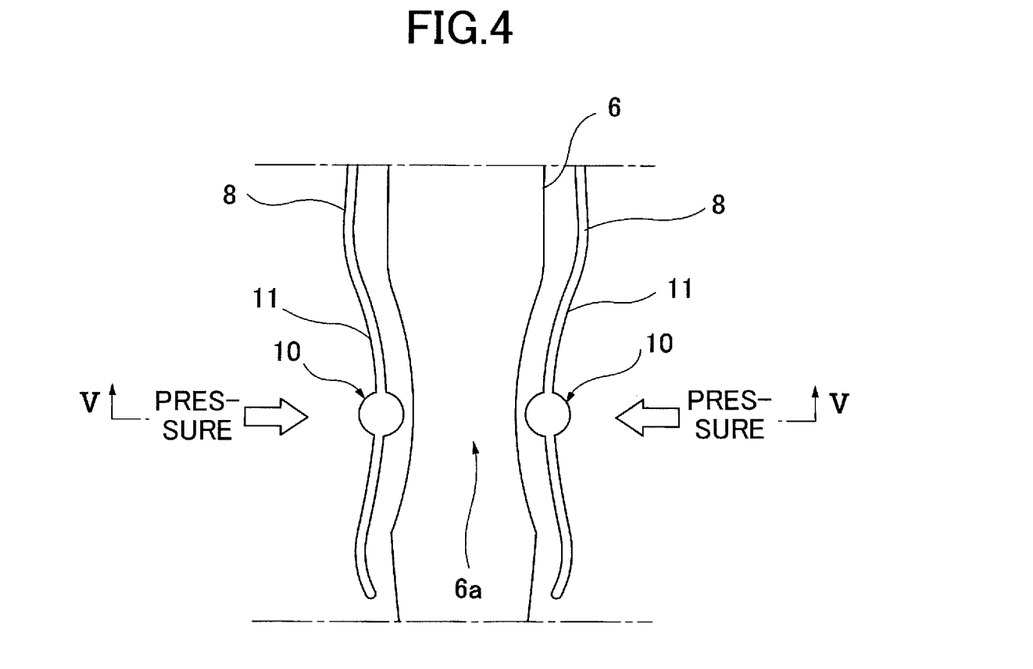
FIG. 4 is an enlarged plan view of the vicinity of vastly enlarged portions 20.
Figure 5:
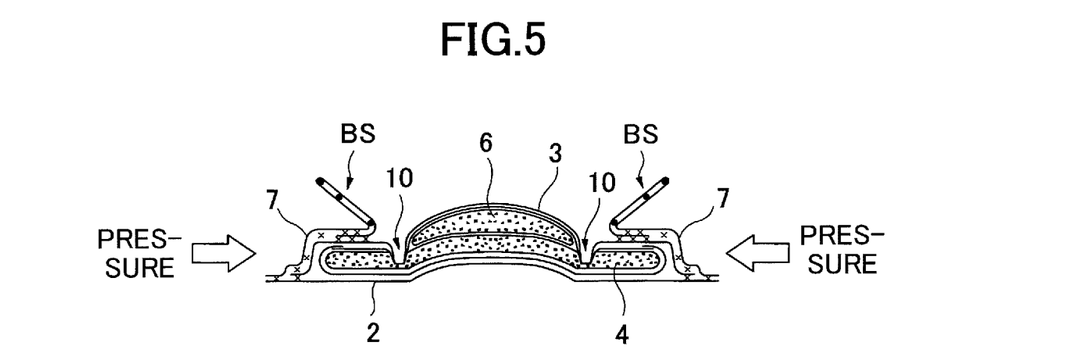
FIG. 5 is a cross-sectional view taken along a line V-V of FIG. 4.

In the sanitary napkin 1, the separation distance reduced regions 11 of the right and left compressed grooves 8, 8 are formed at the back of the region corresponding to the body fluid discharge portion H of the wearer, and also the vastly enlarged portions 10 are formed at positions within the separation distance reduced regions 11 and where a separation distance between the right and left compressed grooves 8, 8 becomes minimum. Therefore, as illustrated in FIG. 4 and FIG. 5, when the leg pressure or the buttocks pressure is exerted from outside to inside in the width direction, pressure tends to be applied to the curved separation distance reduced regions 11 that protrude toward inside in the width direction. Further, the pressure applied to the separation distance reduced regions 11 is concentrated in the vastly enlarged portions 10 that are formed in the minimum distance portions of the separation distance reduced regions 11. The vastly enlarged portions 10 serve as bases for transmitting the pressure to the center portion of the absorbent body 4. Thus, the absorbent body located between the right and left compressed grooves 8, 8 tends to protrude toward the skin side, with the center portion of the absorbent body as the highest point. This center portion protruding toward the skin side makes close contact with the skin surface in the crotch area extending from the body fluid discharge portion H to the start position of the intergluteal cleft of the wearer, allowing body fluids discharged from the body fluid discharge portion H and flowing backward along the skin surface to be securely absorbed. Accordingly, leakage of body fluids from the back can be prevented.

Further, the vastly enlarged portions 10 are formed only in portions of the separation distance reduced regions 11. Thus, it is possible to eliminate discomfort when the sanitary napkin is worn, while also allowing the sanitary napkin 1 not to be prevented from being curved or deformed following the roundness of the body due to the stiffness of the vastly enlarged portions 10.

The number of the vastly enlarged portions 10 formed in each of the separation distance reduced regions 11 of the compressed grooves 8 is preferably 1. When two vastly enlarged portions are provided, pressure for causing the absorbent body 4 located between the right and left compressed grooves 8, 8 to protrude inward may become dispersed. As a result, it may become difficult for the center portion of absorbent body 4 to protrude toward the skin side.

Figure 6:
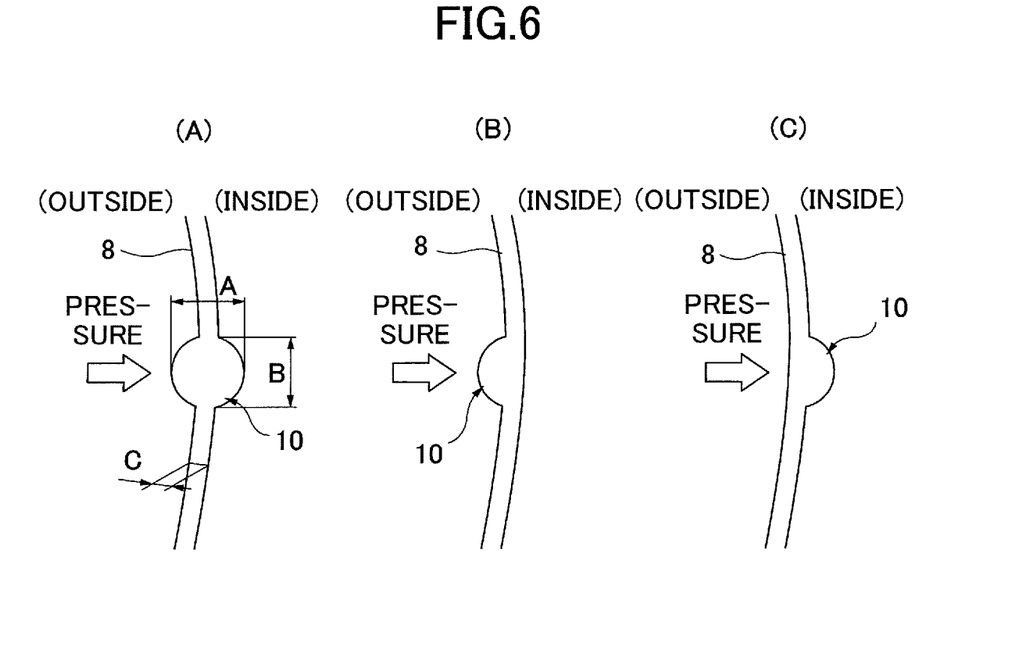

As illustrated in FIG. 6, the vastly enlarged portions 10 may take different shapes. In FIG. 6 (A), the both side walls of the compressed groove 8 are projected outward in the width direction of the groove. In FIGS. 6 (B) and 6 (C), only one of the side walls of the compressed groove 8 is projected outward in the width direction of the groove. More specifically, in the example of FIG. 6 (B), the outer side wall in the width direction of the sanitary napkin 1 is curved. In the example of FIG. 6 (C), the inner side wall in the width direction of the width direction of the sanitary napkin 1 is curved. In the vastly enlarged portion 10, a portion projected toward the outside in the width direction of the sanitary napkin 1 serves to receive leg pressure or buttocks pressure from outside in the width direction, and cause the pressure to be concentrated in the vastly enlarged portion 10. Also, a portion projected toward the inside in the width direction of the sanitary napkin 1, relative to the compressed groove 8 continuing forward and backward, serves as a base for pushing the absorbent body 4 located between the right and left compressed grooves 8, 8 inward. In order to provide the above-described both functions, it is desirable to form the vastly enlarged portion 10 by causing the both side walls of the compressed groove 8 to be projected as illustrated in FIG. 6 (A).

As illustrated in FIG. 6 (A), the vastly enlarged portion 10 may have a size such that a length A in the width direction of the groove and a length B in the longitudinal direction of the groove is twice to eight times longer, and is preferably three times to five times longer than a width C of the compressed groove 8. When the size of the vastly enlarged portion 10 is too small, the vastly enlarged portion 10 does not sufficiently serve as a base for receiving leg pressure and pushing the center portion of the absorbent body inward. When the size of the vastly enlarged portion 10 is too large, pressure for inwardly pushing the center portion of the absorbent body may be dispersed. As a result, there may be a possibility that the center portion of the absorbent body will not readily protrude toward the skin side.

Figure 7:
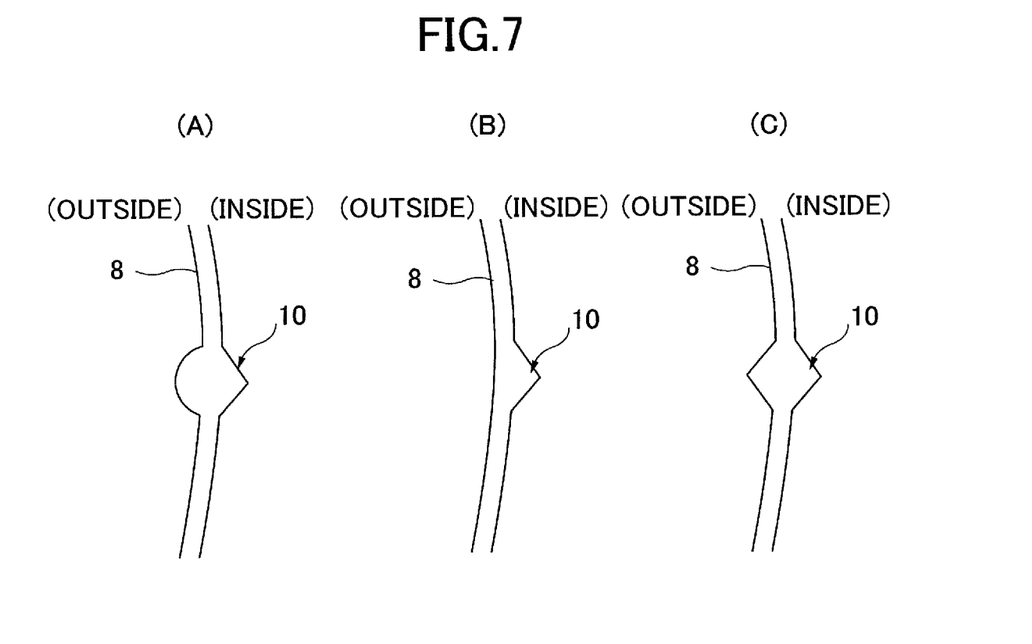

As illustrated in FIG. 6, the shape of the vastly enlarged portion 10 in planar view may be a circular shape or a semicircular shape. Further, as illustrated in FIG. 7, the portion of the vastly enlarged portion 10 projecting inward in the width direction of the sanitary napkin 1 may be formed into a triangle shape with angles. As the center portion of the absorbent body 4 is pushed inward by the triangle-shaped portion, pressure tends to be concentrated. Accordingly, the center portion of the absorbent body 4 readily protrudes further toward the skin side. At this time, the outer side in the width direction of the sanitary napkin 1 may be projected in an arch shape as illustrated in FIG. 7 (A), or is not necessarily projected as illustrated in FIG. 7 (B). Further, as illustrated in FIG. 7 (C), similarly to the projected shape of the inner side, the outer side in the width direction of the sanitary napkin 1 may be projected in a triangle shape with angles, such that the vastly enlarged portion 10 may be formed into an approximately diamond shape or an approximately rectangular shape as a whole.

Second Embodiment

Next, a sanitary napkin 1 according to a second embodiment will be described with reference to FIG. 8 and FIG. 9. In the sanitary napkin 1 according to the second embodiment, a shape of vastly enlarged portions 10 and patterns of compressed grooves formed in the liquid permeable top sheet 3 are different from those of the first embodiment.

Figure 8:
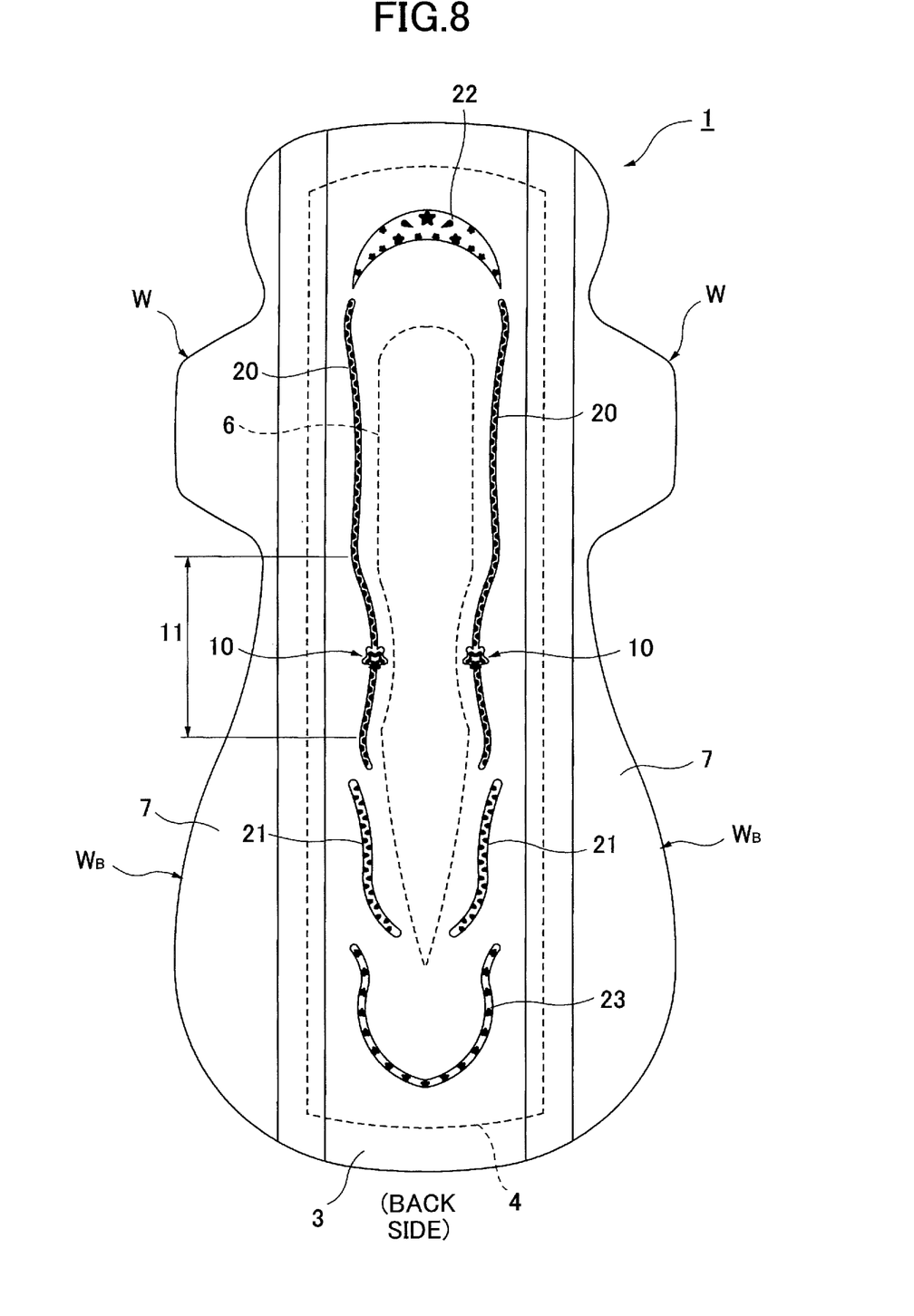
FIG. 8 is an expanded view of a sanitary napkin 1 according to the variation.
Figure 9:
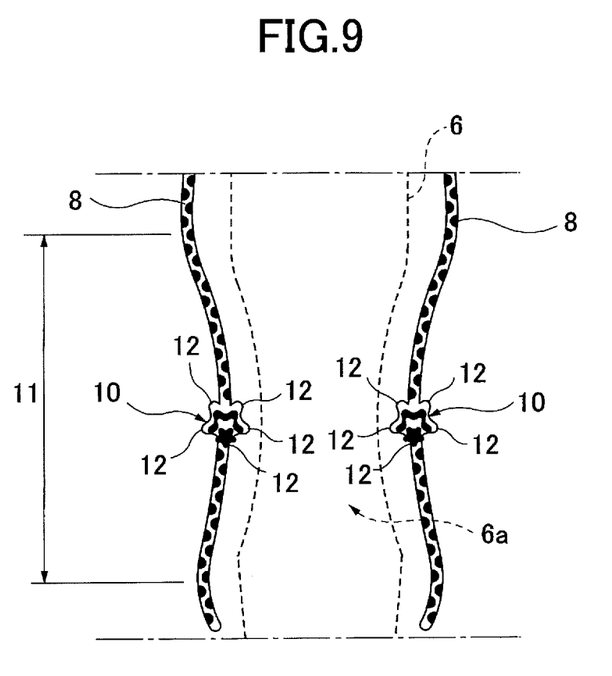
FIG. 9 is an enlarged plan view of the vicinity of the vastly enlarged portions 20.

In the sanitary napkin 1 according to the second embodiment, as illustrated in FIG. 8 and FIG. 9, at least two protruding portions 12, 12 that protrude toward inside in the width direction of the sanitary napkin 1 are provided on the vastly enlarged portion 10. Accordingly, pressure exerted inwardly in the width direction is readily applied in the protruding direction of the protruding portion 12. Thus, an absorbent body 4 located between right and left compressed grooves 8, 8 can be securely pushed inward in the width direction. In the sanitary napkin 1, the at least two protruding portions 12, 12 are disposed adjacent to each other at the front and back. The front protruding portion 12 preferably extends obliquely forward and the back protruding portion 12 preferably extends obliquely backward. Accordingly, pressure for pushing inward is dispersed in the front and back direction, allowing a wider center portion of the absorbent body 4 to protrude toward the skin side. The protruding portion 12 can be similarly formed on the outer side wall in the width direction of the sanitary napkin 1.

Also, by providing two protruding portions on the inner side wall in the width direction, two protruding portions on the outer side wall in the width direction, and one protruding portion on one side in an extending direction of the compressed grooves 8, namely by providing a total of five protruding portions, the vastly enlarged portions 10 may be each formed into an approximately star shape in planar view as a whole. The vastly enlarged portions 10 formed in the approximately star shape firmly receive leg pressure exerted from the outside in the width direction and readily concentrate the pressure in the vastly enlarged portions 10, while also serving as a base for pushing the center portion of the absorbent body 4 inward.

As patterns of the compressed grooves, the sanitary napkin 1 according to the second embodiment includes front-side lengthwise compressed grooves 20, 20 (the same as the compressed grooves 8 according to the first embodiment illustrated in FIG. 1) that are continuously formed on each side extending from the region corresponding to the fluid discharge portion H to the region corresponding to the intergluteal cleft in the approximately longitudinal direction of the sanitary napkin 1, as illustrated in FIG. 1. The sanitary napkin 1 according to the second embodiment also includes back-side lengthwise compressed grooves 21, 21 that are provided at the back away from the front-side lengthwise compressed grooves 20, 20. The back-side lengthwise compressed grooves 21, 21 are continuously formed on each side of a region corresponding to a back end of the intergluteal cleft in the approximately longitudinal direction of the sanitary napkin 1. The sanitary napkin 1 according to the second embodiment also includes a front-end crescent-shaped compressed groove 22 that is provided at the front away from the front-side lengthwise compressed grooves 20, 20, crosses the center line in the longitudinal direction of the sanitary napkin 1, and is formed approximately along the width direction of the sanitary napkin 1. The sanitary napkin 1 according to the second embodiment also includes a back-end curved compressed groove 23 that is provided at the back away from the back-side lengthwise compressed grooves 21, 21, crosses the center line in the longitudinal direction of the sanitary napkin 1, and is curved backward.

As illustrated in the figure, in the front-side lengthwise compressed grooves 20, separation distance reduced regions 11 are formed at the back of the region corresponding to the body fluid discharge portion H of the wearer, and also, the vastly enlarged portions 10 are formed at positions within the separation distance reduced regions 11 and where a separation distance between the right and left compressed grooves becomes minimum.

In the compressed grooves 20 through 23, high compression portions are preferably formed in respective shapes.

DESCRIPTION OF THE REFERENCE NUMERAL 1 sanitary napkin
2 liquid impermeable back sheet
3 liquid permeable top sheet
4 absorbent body
5 encapsulating sheet
6 raised center portion 7 side non-woven fabric
8 compressed groove
9 threadlike elastic expansion and contraction member
10 vastly enlarged portion
11 separation distance reduced region
12 protruding portion
20 front-side lengthwise compressed groove
21 back-side lengthwise compressed groove
22 front-end crescent-shaped compressed groove
23 back-end curved compressed groove

The invention claimed is:

1. An absorbent article comprising,
an absorbent body interposed between a liquid impermeable back sheet and a liquid permeable top sheet, a pair of right and left compressed grooves that extend in an approximately longitudinal direction being formed on a surface of the liquid permeable top sheet so as to sandwich a body fluid discharge portion,
wherein the right and left compressed grooves have a separation distance reduced region, in which a separation distance between the right and left compressed grooves is reduced, formed at back of a region corresponding to a body fluid discharge portion of a wearer, and each of the right and left compressed grooves has only one enlarged portion within its entire length, said only one enlarged portion having an enlarged width of each of the right and left compressed grooves and formed at a position within the separation distance reduced region and where the separation distance between the right and left compressed grooves becomes minimum.

2. The absorbent article according to claim 1, wherein the enlarged portion is formed such that both side walls of each of the compressed grooves are projected outward or only one of the side walls is projected outward.

3. The absorbent article according to claim 1, wherein the enlarged portion has at least two protruding portions that protrude toward inside in a width direction of the absorbent article.

4. The absorbent article according to claim 1, wherein the enlarged portion is formed in an approximately star shape in planar view.

5. The absorbent article according to claim 1, wherein the only one enlarged portion is configured to concentrate, in the only one enlarged portion, pressure applied to the separation distance reduced region from outside to inside in a width direction of the absorbent article.

* * * * *